US009018254B2

(12) United States Patent
Zhang et al.

(10) Patent No.: US 9,018,254 B2
(45) Date of Patent: *Apr. 28, 2015

(54) CYANOACRYLATE TISSUE ADHESIVES WITH DESIRABLE PERMEABILITY AND TENSILE STRENGTH

(71) Applicant: Adhezion Biomedical, LLC, Wyomissing, PA (US)

(72) Inventors: Sheng Zhang, Hickory, NC (US); Rafael Ruiz, Sr., Hudson, NC (US); Max Azevedo, Alpharetta, GA (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/087,693

(22) Filed: Nov. 22, 2013

(65) Prior Publication Data

US 2014/0186289 A1    Jul. 3, 2014

Related U.S. Application Data

(63) Continuation of application No. 13/000,799, filed as application No. PCT/US2009/048234 on Jun. 23, 2009, now abandoned, which is a continuation-in-part of application No. 11/767,565, filed on Jun. 25, 2007, now Pat. No. 8,729,121.

(60) Provisional application No. 61/132,844, filed on Jun. 23, 2008.

(51) Int. Cl.
| A61K 31/275 | (2006.01) |
| A61K 31/785 | (2006.01) |
| A61L 15/24  | (2006.01) |

(52) U.S. Cl.
CPC ............... *A61K 31/785* (2013.01); *A61L 15/24* (2013.01)

(58) Field of Classification Search
None
See application file for complete search history.

(56) References Cited

U.S. PATENT DOCUMENTS

| 211,104 A | 1/1879 | Mulford |
| 334,046 A | 1/1886 | Pinkham |
| 1,221,227 A | 4/1917 | Schulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |
| 3,742,018 A | 6/1973 | O'Sullivan |
| 3,779,706 A | 12/1973 | Nabio |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |
| 3,924,623 A | 12/1975 | Avery |
| 3,941,488 A | 3/1976 | Maxwell |
| 3,975,422 A | 8/1976 | Buck |
| 3,995,841 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |

(Continued)

FOREIGN PATENT DOCUMENTS

| DE | 2010 3336 | 5/2001 |
| EP | 0127466 | 12/1984 |

(Continued)

OTHER PUBLICATIONS

"Answer and Counterclaim", *Adhezion Biomedical, LLC v. Max Azevedo*, Civil Action No. 13-CVS-191, State of North Carolina, Superior Court Division, Mar. 20, 2013, 16 pages.
"Complaint", *Adhezion Biomedical, LLC v. Max Azevedo*, Civil Action No. 13-CVS-191, State of North Carolina, Superior Court Division, filed Feb. 13, 2013, 17 pages.
"First Amended Answer And Counterclaim", *Adhezion Biomedical, LLC v. Max Azevedo*, Civil Action No. 13-CVS-191, State of North Carolina, Superior Court Division, Apr. 29, 2013, 17 pages.
"Reply And Defenses To Counterclaim" *Adhezion Biomedical, LLC v. Max Azevedo*, Civil Action No. 13-CV-191, State of North Carolina, Superior Court Division, Jun. 3, 2013, 12 pages.
"Consent Judgment", *Adhezion Biomedical, LLC v. Max Azevedo*, Civil Action No. 13-CV-191, State of North Carolina, Superior Court Division, Jul. 24, 2013, 7 pages.

(Continued)

*Primary Examiner* — Susan Tran
*Assistant Examiner* — Jessica Worsham
(74) *Attorney, Agent, or Firm* — Baker & Hostetler LLP

(57) ABSTRACT

A sterilized cyanoacrylate adhesive composition including a cyanoacrylate composition and a cure speed enhancer, wherein said sterilized cyanoacrylate adhesive composition does not cure upon sterilization, and wherein the composition when cured to form a film on a patient's tissue has water vapor transmission rate from about 950 to about 3000 g/m²/day.

16 Claims, No Drawings

(56) References Cited

U.S. PATENT DOCUMENTS

| | | |
|---|---|---|
| 4,102,945 A | 7/1978 | Gleave |
| 4,105,715 A | 8/1978 | Gleave |
| 4,109,037 A | 8/1978 | Nohara |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,265,948 A | 5/1981 | Hayes et al. |
| 4,310,509 A | 1/1982 | Berglund et al. |
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |
| 4,377,490 A | 3/1983 | Shiraishi et al. |
| 4,386,193 A | 5/1983 | Reich et al. |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,713,235 A | 12/1987 | Krall |
| 4,718,966 A | 1/1988 | Harris et al. |
| 4,772,148 A | 9/1988 | Buschemeyer |
| 4,786,534 A | 11/1988 | Aiken |
| 4,818,325 A | 4/1989 | Hiraiwa et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,994,542 A | 2/1991 | Matsuda et al. |
| 5,009,654 A | 4/1991 | Minshall et al. |
| 5,039,753 A | 8/1991 | Woods et al. |
| 5,042,690 A | 8/1991 | O'Meara |
| 5,051,256 A | 9/1991 | Barnes |
| 5,069,907 A | 12/1991 | Mixon et al. |
| 5,083,685 A | 1/1992 | Amemiya et al. |
| 5,131,777 A | 7/1992 | Kimura et al. |
| 5,135,964 A | 8/1992 | Lee et al. |
| 5,167,616 A | 12/1992 | Haak et al. |
| 5,169,383 A | 12/1992 | Gyory et al. |
| 5,192,536 A | 3/1993 | Huprich |
| 5,225,182 A | 7/1993 | Shamna |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,530,037 A | 6/1996 | McDonnell et al. |
| 5,547,662 A | 8/1996 | Khan et al. |
| 5,561,198 A | 10/1996 | Huver et al. |
| 5,665,817 A | 9/1997 | Greff et al. |
| 5,684,042 A | 11/1997 | Greff et al. |
| 5,730,994 A | 3/1998 | Askill et al. |
| 5,749,956 A | 5/1998 | Fisher et al. |
| 5,762,919 A | 6/1998 | Greff et al. |
| 5,783,177 A | 7/1998 | Greff et al. |
| 5,803,086 A | 9/1998 | Scholz et al. |
| 5,807,563 A | 9/1998 | Askill et al. |
| 5,811,091 A | 9/1998 | Greff et al. |
| 5,874,044 A | 2/1999 | Kotzev |
| 5,902,594 A | 5/1999 | Greff et al. |
| 5,916,882 A | 6/1999 | Jeng |
| 5,928,611 A | 7/1999 | Leung |
| 5,944,754 A | 8/1999 | Vacanti |
| 5,957,877 A | 9/1999 | Askill et al. |
| 5,979,450 A | 11/1999 | Baker et al. |
| 5,981,621 A | 11/1999 | Clark et al. |
| 5,985,395 A | 11/1999 | Comstock et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,214,332 B1 | 4/2001 | Askill et al. |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,316,523 B1 | 11/2001 | Hyon et al. |
| 6,323,275 B2 | 11/2001 | Takahashi et al. |
| 6,352,704 B1 | 3/2002 | Nicholson et al. |
| 6,488,665 B1 | 12/2002 | Severin et al. |
| 6,492,434 B1 | 12/2002 | Bartey, Jr. et al. |
| 6,495,229 B1 | 12/2002 | Carte et al. |
| 6,547,917 B1 | 4/2003 | Misiak et al. |
| 6,579,469 B1 | 6/2003 | Nicholson et al. |
| 6,620,846 B1 | 9/2003 | Jonn et al. |
| 6,626,296 B1 | 9/2003 | Jimu et al. |
| 6,667,031 B2 | 12/2003 | Azevedo |
| 6,699,940 B2 | 3/2004 | Shalaby |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B2 | 9/2004 | Kotzey |
| 6,802,416 B1 | 10/2004 | D'Aiessio et al. |
| 6,849,082 B2 | 2/2005 | Azevedo |
| 6,881,421 B1 | 4/2005 | DaSilveira |
| 6,896,838 B2 | 5/2005 | D'Aiessio |
| 6,942,875 B2 | 9/2005 | Hedgpeth |
| 6,960,040 B2 | 11/2005 | D'Aiessio et al. |
| 6,974,585 B2 | 12/2005 | Askill |
| 6,977,278 B1 | 12/2005 | Misiak |
| 6,995,227 B2 | 2/2006 | Ryan et al. |
| 7,255,874 B1 | 8/2007 | Bobo et al. |
| 8,287,901 B2 | 10/2012 | Zhang et al. |
| 8,293,838 B2 | 10/2012 | Zhang et al. |
| 2002/0002223 A1 | 1/2002 | Cox et al. |
| 2002/0037272 A1 | 3/2002 | Askill et al. |
| 2003/0044380 A1 | 3/2003 | Zhu et al. |
| 2003/0077386 A1 | 4/2003 | Azevedo |
| 2003/0135016 A1 | 7/2003 | Tajima et al. |
| 2003/0158579 A1 | 8/2003 | Azevedo |
| 2003/0158580 A1 | 8/2003 | Azevedo |
| 2004/0115274 A1 | 6/2004 | Cox et al. |
| 2004/0126355 A1 | 7/2004 | Childers |

(56) References Cited

U.S. PATENT DOCUMENTS

| | | | |
|---|---|---|---|
| 2004/0127738 A1 | 7/2004 | Azevedo |
| 2004/0253039 A1 | 12/2004 | Stenton |
| 2005/0042266 A1 | 2/2005 | Narang |
| 2005/0047846 A1 | 3/2005 | Narang et al. |
| 2005/0067312 A1 | 3/2005 | Gupta et al. |
| 2005/0142163 A1 | 6/2005 | Hunter et al. |
| 2005/0147582 A1 | 7/2005 | Zimmerman et al. |
| 2005/0182347 A1 | 8/2005 | Bishop et al. |
| 2005/0196431 A1 | 9/2005 | Narang et al. |
| 2005/0197421 A1 | 9/2005 | Loomis |
| 2005/0281866 A1 | 12/2005 | Jarrett et al. |
| 2005/0284487 A1 | 12/2005 | Gellerstedt et al. |
| 2006/0062687 A1 | 3/2006 | Morales |
| 2006/0188486 A1 | 8/2006 | Carpenter et al. |
| 2007/0041935 A1 | 2/2007 | Salamone et al. |
| 2007/0048356 A1 | 3/2007 | Schorr et al. |
| 2007/0078207 A1 | 4/2007 | Jonn et al. |
| 2007/0092481 A1 | 4/2007 | Misiak et al. |
| 2007/0092483 A1 | 4/2007 | Pollock |
| 2007/0147947 A1 | 6/2007 | Stenton et al. |
| 2007/0299043 A1 | 12/2007 | Hunter et al. |
| 2008/0021139 A1 | 1/2008 | Blacklock et al. |
| 2008/0078413 A1 | 4/2008 | Padget et al. |
| 2008/0102053 A1 | 5/2008 | Childers |
| 2008/0319063 A1 | 12/2008 | Zhang |
| 2009/0022779 A1 | 1/2009 | Kelly et al. |
| 2009/0317353 A1 | 12/2009 | Zhang et al. |
| 2010/0035997 A1 | 2/2010 | Broadley et al. |
| 2010/0269749 A1 | 10/2010 | Badejo et al. |

FOREIGN PATENT DOCUMENTS

| | | |
|---|---|---|
| EP | 0271675 | 6/1988 |
| FR | 2700698 | 7/1994 |
| GB | 1230560 | 5/1971 |
| GB | 2200124 | 7/1988 |
| JP | 59-066471 | 4/1984 |
| JP | 62-022877 | 1/1987 |
| JP | 03-207778 | 9/1991 |
| JP | 10-140091 | 5/1998 |
| WO | WO 96/14292 | 5/1996 |
| WO | WO 96/23532 | 8/1996 |
| WO | WO 99/10020 | 3/1999 |
| WO | WO 03/070257 | 8/2003 |
| WO | WO 2004/045498 | 6/2004 |
| WO | WO 2006/073922 | 7/2006 |
| WO | WO 2009/003017 | 12/2008 |
| WO | WO 2009/064291 | 5/2009 |

OTHER PUBLICATIONS

Bhatia et al, "Topical Phenytoin for Wound Healing" Dermatology Online Journal, 10(1): 5 (2004) 6 pages as downloaded from http://dermatology-s.cdlib.org/101/reviews/phenytoin/bhatia.html.

http://www.merriam-webster.com/dictionary/kit, Retrieved on Aug. 25, 2011.

International Search Report and Written Opinion issued Jan. 9, 2012 for corresponding international patent application No. PCT/US2011/047090.

Naeini et al, "Effects of Topical and Parenteral Application of Phenytoin on Cutaneous Wound Healing in Rabbits" in Journal of Animal and Veterinary Advances 2008, 7(12),1537-1545.

Pendse et al, "Topical Phenytoin in Wound Healing" International Journal of Dermatology, Mar. 1993, 32(3), 214-217.

Quinn et al, "A Randomized Trial Comparing Octylcyanoacrylate Tissue Adhesive and Sutures in the Management of Lacerations" JAMA, May 21, 1997, 277(19),1527-1530.

Scheinfeld, "Phenytoin in Cutaneous Medicine: Its Uses, Mechanisms and Side Effects" Dermatology Online Journal, 2003, 9(3), 17pages downloaded from http://dermatology-s10.cdlib.org/93/reviews/dilantin/scheinfeld.html.

Shapiro, "Acceleration of Gingival Wound Healing in Non-Epileptic Patients Receiving Diphenylhydantoin Sodium (Dilantin, Epanutin)" in Exp. Med. Surg. 1958, 16(1), 41-53.

Simon et al, "Lacerations Against Langer's Lines: To Glue or Suture" in Journal of Emergency Medicine, 1998, 16(2),185-189.

Talas et al, "Role of Phenytoin in Wound Healing—A Wound Pharmacology Perspective" in Biochemical Phannacology, May 1999, 57, 1085-1094.

Aclar®/Barex® Laminates: Flexible Solutions for Pharma PackagingDrug Delivery Technology, 3(3), May 2003, Posted on Mar. 28, 2008, http://www.drugdelivmtech.com/ME2/dirmod.as/l?sid=&nrn=&tme=Publishing
&rnod=Publications%3A%3AArticle
&mid=8F3A7027421841978FI8BE895F87F79I&tier=4&id-6EC6964EB29D46D8A297E499E57A4164.

Cameron, J.L. et al., "The Degradation of Cyanoacrylate Tissue Adhesive, pt. 1", Surgery, 58(2), 232 Aug. 1965, 424-430.

Collins et al., "Biological Substrates and Cure Rates of Cyanoacrylate Tissue Adhesives" Archives of 233 Surgery, 93, Sep. 1966, 428-432.

Darwish et al., "The evaluation of Crown Ether Based Niosomes As Cation Containing And Cation Sensitive 234 Drug Delivery Systems" International Journal Of Pharmaceutics 159, 1997, 207-213.

Dumont et al., "New Oligosaccharidic Crown Ethers as Potential Drug-Targetting Vectors: Synthesis & 235 Biological Evaluation" Bioorganic & Medicinal Chemistry Letters, 1994, 4(9), 1123-1126.

Fussnegger, B. UPoloxamers (1) Lutrol® F 68 (Poloxamer 188). BASF ExAct, No. 3, Nov. 1999, 236, 5-6.

Garnier-Suillerot et al., "Analysis of Drug Transport Kinetics in Multidrug-Resistant Cells: Implications for 237 Drug Action" Current Medicinal Chemistry, 2001, 8, 51-64.

Hansen, "Fast Cure—High Moisture Vapor Transmission Rate Adhesives Improve Wound Care." Adhesives 238 Age, Mar. 2003, pp. 22, 24 and 25.

InternationalSearch Report and Written Opinion dated Aug. 4, 2010 for international application No. PCT/US2009/048234.

Lehman et al., "Toxicity of Alkyi2-Cyanoacrylates", Archives of Surgery, Sep. 1966, 93(3), 441-446.

Leonard, F, "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Aikyl a-Cyanoacrylate Homologs", Journal of Applied Polymer Science, 10, 1966, 1617-1623.

Leonard, F. et al.,"Synthesis and Degradation of Poly (alkyl a-Cyanoacrylates)", Journal of Applied Polymer Science, 10(8), Aug. 1966, 1214.

Leonard, F. et al., "Synthesis and Degradation of Poly(alkyl a-Cyanoacrylates}", Journal of Applied Polymer Science, 10(2), Feb. 1966, 259-272.

Material Safety Data Sheet (MSDS) of isobuthyl-2-cyanoacrylate; Sep. 25, 1998.

Material Safety Data Sheet {MSDS} of 2-octyl cyanoacrylate; Jun. 2, 2004.

Material Safety Data Sheet {MSDS) of n-butyl cyanoacrylate; Oct. 19, 2009 and Jun. 2, 2004.

Sorrel et al. "The Effect of Crown Ethers, Tetraalkylammonioum Salts, and Polyoxyethylene Amphiphiles 231 on Pirarubicin Incorporation in K562 Resistant Cells" Biochemical Pharmacology,1995, 50(12), 2069-2076, Borrel et al.

Tseng, Y.C. et al., "Modification of Synthesis And Investigation Of Properties for 2-Cyanoacrylates", Biomaterials, 11, Jan. 1990, 73-79.

Uchegbu et al., "Non-ionic Surfactant Based Vesicles (niosomes) in Drug Delivery" International Journal of Pharmaceutics, 1998, 172, , 33-70.

Vezin, W.R et al.. "Diffusion of Small Molecules in Poly-n-Aikyl Cyanoacrylates", British Pharmaceutical Conference 1978—Communications presented at the 115th meeting, Coventry, Sep. 11-15, 1978, Journal of Pharmacy and Pharmacology, 30, Suppl, Dec. 1978, p. 2P.

Vezin, W.R. et al., "In Vitro Heterogeneous Degradation Of Poly(n-alkyl a-cyanoacrylates)", Journal of Biomedical Materials Research,14, 1980, 93-106.

Woodward, S.C. et al., "Histotoxicity of Cyanoacrylate Tissue Adhesives in the Rat", Annals of Surgery, 252, 162(1), Jul. 1965, 113-122.

Yonezawa, M. et al., "Studies on a-Cyanoacrylate, VI: Reaction of Cyanoacetate with Formaldehyde" 253 Yuki Gosei Kagaku Kyokaishi, 25(4), Apr. 1967, 311-316.

CYANOACRYLATE TISSUE ADHESIVES WITH DESIRABLE PERMEABILITY AND TENSILE STRENGTH

CROSS REFERENCE TO RELATED APPLICATIONS

This application is a continuation of pending U.S. patent application Ser. No. 13/000,799, filed Dec. 22, 2010, which is a U.S. National Stage Application of International Application No. PCT/US2009/048234, which claims benefit of U.S. patent application Ser. No. 61/132,844, filed on Jun. 23, 2008, the disclosures of which are incorporated herein by reference in their entirety. PCT/US2009/048234 is also a continuation-in-part of U.S. patent application Ser. No. 11/767,565, filed on Jun. 25, 2007, the disclosure of which is incorporated herein by reference in its entirety.

BACKGROUND OF THE INVENTION (1) Field of the Invention

The present invention relates to cyanoacrylate adhesives. In particular, the present invention relates to cyanoacrylate adhesives with an enhanced cure speed for medical use and that, once cured, exhibit improved permeability and mechanical properties such as, for example, wound closure strength, overlap shear strength, peel adhesive strength, and flexibility.

(2) Description of Related Art

Cyanoacrylate compositions have long been known in the art as excellent adhesives. The cyanoacrylate adhesives are liquid monomers that polymerize on contact with tissue surfaces in an exothermic reaction creating a strong yet flexible film. The polymer film is generally formed rapidly. Liquid cyanoacrylate compositions have found application in medicine for closing wounds and incisions, especially in cases where suturing does not provide satisfactory results because of cyanoacrylates unique ability to bond living tissue and their long-term bond strength. They have found wide applications as industrial and structural adhesives, consumer products for repair of household items and in the hobby sector for assembly and repair.

It is well known that cyanoacrylate adhesive compositions are very sensitive and careful handling is required to prepare their formulations. In order to extend the applications of cyanoacrylate adhesives, a variety of additives have been incorporated in their formulations including stabilizers, viscosity modifiers, thixotropic agents, plasticizers, biocompatible agents, and polymerization activators.

Cyanoacrylate polymerization is usually considered as the result of an anionic initiation with water being a sufficiently strong base. In spite of the relatively fast cure speed of cyanoacrylate adhesives, polymerization enhancers have to be incorporated for specific applications. First, the cure speed would be drastically dropped if cyanoacrylate adhesives were applied to acidic substrates such as wood and paper. In this case, the cyanoacrylate adhesives with a faster cure time would offer an option. In addition, a relatively large amount of cyanoacrylate applied in certain cases will result in the slower hardening throughout the adhesives.

In order to enhance the polymerization rate for such applications, a number of efforts have been made by applying accelerators through different methods. For example, a two component system has been used by packaging the cyanoacrylate adhesive and the accelerator separately. The cure speed of cyanoacrylate adhesives is improved. The disadvantage of this method is that the accurate measurement and mixing two components homogeneously are very difficult tasks to achieve since only a tiny amount of accelerators is generally required.

As an example, U.S. Pat. No. 5,928,611 to Leung discloses an applicator tip for dispensing a polymerizable material, in which a polymerization accelerator was included. The accelerator initiates polymerization when the polymerizable material is dispensed through the applicator tip. Suitable accelerators include detergent compositions; surfactants, amines, urea, phosphines, alcohols, inorganic bases and salts, sulfur compounds, polymeric cyclic ethers, crown ethers, calixarenes, cyclic and acyclic carbonates, organometallics, and radical. The polymerizable material may also contain an initiator which is inactive until activated by a catalyst in the applicator tip. Initiators activated by stimulation such as heat and/or light are also suitable if the tip and/or applicator is appropriately subjected to such stimulation.

U.S. Pat. Application No. 20050196431 to Narang et al. discloses an applicator tip for an applicator for applying a polymerizable monomeric adhesive composition that can include a bioactive material, a flavorant, a polymerization initiator, and/or a polymerization rate modifier. It has been discovered that the use of methanol, alone or as a component of a mixture of low boiling point solvents, to apply a polymerization accelerator to an applicator tip used to dispense monomer-containing adhesive compositions, provides an unexpectedly superior distribution profile of the material on, and within, the applicator tip. Applicator tips according to their invention can control the setting time of the polymerized or cross-linked adhesive, extend the shelf life of the monomer and control the flow properties of applied cyanoacrylate adhesives.

U.S. Pat. No. 4,460,759 to Narang discloses two-component adhesive compositions. One component contains the cyanoacrylate monomer and the second component contains a weakly acidic or weakly basic ionic accelerator consisting of a cation having a pKa of at least 10 and a nucleophilic anion.

Another approach to enhance the cure speed of cyanoacrylate adhesive is to apply the diluted solutions of the accelerators in low-boiling point solvents to the cyanoacrylate adhesives. The accelerator solutions can be added to the substrate in advance or applied when the cyanoacrylate adhesive is still liquid. Japanese Patent Application No. JP-A-03 207 778 discloses the use of solutions of aliphatic, alicyclic and, especially, tertiary aromatic amines as the activators for the curing of cyanoacrylate adhesives. Specific examples included N,N-dimethylbenzylamine, N-methylmorpholine and N,N-diethyltoluidine. Japanese Patent Application No. JP-A-62 022 877 suggested the use of solutions of lower fatty amines, aromatic amines, and dimethylamine for the same purpose.

British Patent Specification No. 1 230 560 described cyanoacrylate adhesive compositions containing certain substituted heterocyclic compounds as accelerators. The compositions may be presented in a two-part form, the first part comprising the cyanoacrylate adhesive and the second part comprising at least one of the substituted heterocyclic compounds, preferably dissolved in an organic solvent. The heterocyclic compound is invariably present in one part of a two-part composition because iminoethylene-substituted triazines and pyrimido-pyrimidines accelerate the polymerization so rapidly that they must be kept apart from the cyanoacrylate composition before use. An effective adhesive bond is obtained. However it is not concerned with an activator which is able to initiate polymerization throughout a layer of adhesive.

U.S. Pat. No. 3,260,637 to von Bramer discloses the use of a range of organic amines as accelerators for cyanoacrylate adhesives, particularly for use on metallic and non-metallic substrates. According to the invention, a catalyst solution comprising one or more organic amines was employed in a suitable solvent to moisten the surfaces to be bonded and to catalyze the adhesive action of cyanoacrylate adhesive composition.

U.S. Pat. No. 4,042,442 to Dombroski et al. discloses the addition of a polymerization initiator such as caffeine and theobromine to a cyanoacrylate adhesive composition. The caffeine or theobromine is added to the adhesive composition in different ways. Firstly, the caffeine or theobromine is dissolved in a volatile solvent, applied to the surfaces to be joined, the volatile solvent is allowed to evaporate, and then the cyanoacrylate adhesive composition is applied to the surfaces of the substrates to be joined. Secondly, the caffeine or theobromine can be mixed with the cyanoacrylate adhesive composition by stirring just prior to application of the adhesive to the substrates to be joined. Both of these methods are inconvenient for the user because two separate solutions or two separate applications are required.

U.S. Pat. No. 5,561,198 to Huver provided an activator for cyanoacrylate adhesives based on N,N-dialkyl aniline derivatives. The activators are characterized by a molecular weight of more than 200 and by at most 3 carbon atoms for both N,N-dialkyl substituents together. Their invention also provided methods of production and use of the activator and to the combination product of the activator and the cyanoacrylate adhesive. In their inventions, the activators were tested according to criteria including reactivity, cure rate on activated aluminum test strips, cure rate after activation, tensile shear strength on sand-blasted aluminum strips, transparency, and odor of the reactivity.

U.S. Pat. No. 6,547,917 to Hanns et al. revealed the accelerated curing of cyanoacrylate adhesives using organic compounds containing the structural element —N═C—S—S—C═N— in dilute solution as activators. Examples of such compounds include 6,6'-dithiodinicotinic acid, dibenzodiazyl disulfide, 2,2'-dipyridyl disulfide or bis(4-t-butyl-1-isopropyl-2-imidazolyl)disulfide. According to their invention, the activators are dissolved in readily volatile solvents, such as hydrocarbons, carboxylic acid esters, ketones, ethers or halogenated hydrocarbons. The activator solutions according to their invention are suitable for the accelerated curing of all conventional cyanoacrylate adhesives which contain as the fundamental constituent one or more cyanoacrylic acid esters, inhibitors of free-radical polymerization, inhibitors of anionic polymerization and, optionally, conventional auxiliary substances employed in such adhesive systems. As compared with the known accelerators, their method provided the following advantage: good accelerating action, but they nevertheless require a long waiting time between application of the activator and application of the adhesive.

U.S. Pat. No. 6,995,227 to Ryan et al. discloses an activator composition for the accelerated curing of cyanoacrylate adhesives, wherein the activator comprises a member selected from the group consisting of: aromatic heterocyclic compounds having at least one N hetero atom in the ring(s) such as pyridines, quinolines and pyrimidines and substituted on the ring(s) with at least one electron-withdrawing group which decreases the base strength of the substituted compound compared to the corresponding unsubstituted compound, mixtures of any of the foregoing with each other, and/or with N,N-dimethyl-p-toluidine, and mixtures of any of the foregoing and/or N,N-dimethyl-p-toluidine with an organic compound containing the structural element, such as dibenzothiazyl disulfide, 6,6'-dithiodinicotinic acid, 2,2'-dipyridyl disulfide, and bis(4-t-butyl-1-isopropyl-2-imidazolyl)disulfide. An activator composition may comprise a solution of one or more activators in a solvent mixture which comprises a volatile hydrocarbon and a cyclic ketone. Their invention reduced the problem of "halo" effect and provided activator solutions with different properties.

In order to improve the cure speed of cyanoacrylate adhesives, another important method is to incorporate accelerators directly to the adhesive formulations. DE-A40 09 621 proposed the use of certain cyclodextrine derivatives as an additive to improve the cure speed of cyanoacrylate adhesive, some of which are soluble in cyanoacrylates. GB-A-2 200 124 revealed the use of acyclic phenol-formaldehyde oligomers as an accelerating additive for cyanoacrylate adhesive formulations.

German patent DE-A-22 61 261 proposed accelerator substances containing the structural element —N═C—S—. According to their invention, cyanoacrylate adhesives containing such accelerators do in fact show that even relatively large amounts of adhesive harden relatively rapidly and reliably. However, that compound has a very high volatility, so that activator solutions based thereon are unsuitable for application beforehand since the active ingredient also evaporates off with the solvent.

U.S. Pat. No. 4,386,193 to Reich, et al. discloses a rapid-setting α-cyanoacrylate based adhesive composition having good storage stability and, in particular, to an adhesive composition having a very fast setting time on wood and other substrates with a porous/acid surface by using 3 or 4 arm polyol podand compounds as accelerators.

Japanese Patent Application No. 59-66471 discloses amine derivatives as a curing accelerator of cyanoacrylate adhesives. The amine compounds have a boiling point of between 50° C. and 250° C. Examples of suitable amines include propanolamine triethyl amine, diethyl amine, isopropyl amine, butyl amine, tributyl amine, N,N-dimethyl-o-toluidine, N,N-dimethyl aniline, N,N-diethyl aniline, N,N-dimethyl-p-toluidine, N,N-dimethyl-m-toluidine dimethyl benzyl amine, pyridine, picoline, vinyl pyridine, ethanolamine, and ethylene diamine.

U.S. Pat. No. 4,377,490 to Shiraishi et al., discloses mixtures of aromatic and aliphatic polyols and polyethers to improve initial strength of cyanoacrylate wood bonding products.

European Patent Specification No. 0 271 675 A2 discloses a primer for cyanoacrylate resin compositions for use in bonding non-polar or highly crystallized resins such as polyolefins, polyethyleneterephthalates, nylons, fluorine-containing resins, and soft PVC films. The primer comprises (i) an organic amine and (ii) a compound selected from the group consisting of benzene ring compounds having aldehyde group and nitrogen or oxygen atom-containing heterocyclic compounds having aldehyde group. The specification states that a cyanoacrylate adhesive exhibited a strong bonding strength at ambient temperature.

U.S. Pat. No. 4,718,966 to Stephen, et al. discloses cyanoacrylate adhesive compositions which employ calixarene compounds as accelerators give substantially reduced fixture and cure times on deactivating substrates such as wood, leather, ceramic, plastics and metals. The calixarene compounds are preferably employed at levels of about 0.1-1% by weight of the composition.

In U.S. Pat. No. 4,170,585 to Motegi et al., certain polyethylene glycols poly(ethyleneoxy) functional are disclosed to be additives for increasing the curing speed of cyanoacrylate compositions. Such compounds, however, have the reported disadvantage that they contain water and other substances difficult to remove which spontaneously initiate polymerization of the cyanoacrylate monomer.

Japanese Patent Application No. 8-310136 to Ohashi, et al. discloses 2-cyanoacrylate adhesive compositions containing a crown ether curing accelerator or a polyalkylene oxide curing accelerator. However, these compositions are not suitable for medical applications.

In general, cyanoacrylate combinations with accelerators have been obtainable by separately housing the cyanoacrylate and accelerator. The cyanoacrylate is then flowed past the accelerator housing to add the accelerator to the cyanoacrylate. This method is used for industrial applications, where large batches of the cyanoacrylate are needed. This method is not suitable for medical use, nor are the cyanoacrylate compositions prepared from this method amenable to being sterilized in preparation for medical use.

Based on the descriptions above, different design systems and a variety of chemicals have been applied to accelerate the curing speed of cyanoacrylate adhesives. However, most of the employed accelerators exhibited their own shortcomings at different extents. Some of them are more toxic, while others exhibit weak activation, less bond strength, high volatility and odor. In addition, irregular structure is formed in some cases, which destroys transparency of film. These disadvantages thus limit the application of cyanoacrylate adhesives in different fields, especially for medical use.

Moreover, in spite of the fact that many cyanoacrylate compositions have been disclosed for surgical wound dressing and management, none of the prior art cyanoacrylate-based surgical adhesives exhibit a desirable permeability or breathability. However, permeability, as measured by moisture vapor transmission rate (MVTR), is a desirable characteristic of a surgical adhesive because it prevents maceration of the skin due to trapped moisture, improve wound healing, and to enhance patient's comfort during wear of the bandage. Desirable permeability can provide the following benefits: (1) removing and preventing exudates from pooling while keeping the wound moist during the process of wound healing, (2) permitting appropriate oxygen ingress and carbon dioxide egress, and (3) minimizing the formation of trauma to surrounding or new tissue.

It has been reported that adhesives with high moisture vapor transmission rate improve wound care (Hansen et al. *Adhesive Age* 22-25, 2003). The prior art has emphasized the importance of permeability of wound dressing products on the wound healing process. For example, U.S. Pat. No. 4,649,909 to Thompson teaches a wound dressing made of polyurethane film. The moisture vapor transmission feature of the dressing film contributes to the improved wound healing. U.S. Pat. No. 6,495,229 to Carte et al. provides a method of speeding the healing of wounds using a rubber-based or acrylic pressure-sensitive adhesive bandage with high moisture vapor transmission rate. U.S. Pat. Appl. No. 20050182347 to Bishop et al. claims a multi-layered wound dressing comprising a layer having a high moisture vapor transmission rate (MVTR). The wound dressing possesses improved fluid handling capacity and high MVTR to reduce maceration of the surrounding skin and prevent wound desiccation.

Accordingly, there is a need in the art for a cyanoacrylate adhesive composition with a polymerization accelerator, which provides a desirable permeability or breathability for improved wound healing.

SUMMARY OF THE PRESENT INVENTION

In one aspect, the present invention provides a sterilized cyanoacrylate adhesive composition including a cyanoacrylate composition and a cure speed enhancer, wherein said sterilized cyanoacrylate adhesive composition does not cure upon sterilization, and wherein the composition when cured to form a film on a patient's tissue has water vapor transmission rate from about 950 to about 3000 $g/m^2/day$.

In another aspect, the present invention provides a method of sealing tissue, including the steps of: applying the sterilized cyanoacrylate adhesive composition as a liquid to a patient's tissue to be sealed; and curing the sterilized cyanoacrylate adhesive composition to seal the patient's tissue, wherein the composition when cured to form a film on the patient's tissue has water vapor transmission rate of from about 950 to about 3000 $g/m^2/day$.

DETAILED DESCRIPTION OF THE INVENTION

The present invention provides a sterilized cyanoacrylate adhesive composition and method of preparing the same including a cure speed enhancer added to a cyanoacrylate adhesive composition. The sterilized cyanoacrylate adhesive composition is essentially a bioabsorbable tissue adhesive for sealing and aiding in the repair of tissue. Importantly, the sterilized cyanoacrylate adhesive composition does not cure upon sterilization and, when cured, provides an advantageous quantity of permeability.

The compositions of the present invention comprise cyanoacrylate monomers. Such cyanoacrylate monomers are readily polymerizable, e.g., anionically polymerizable or free radical polymerizable. Cyanoacrylate monomers suitable for use in accordance with the present invention include, but are not limited to, 1,1-disubstituted ethylene monomers of the formula:

$$HRC=CXY \qquad (I)$$

wherein X and Y are each strong electron withdrawing groups, and R is H, —CH=$CH_2$, or a $C_1$-$C_4$ alkyl group.

Examples of monomers within the scope of formula (I) include alpha-cyanoacrylates, vinylidene cyanides, $C_1$-$C_4$ alkyl homologues of vinylidene cyanides, dialkyl methylene malonates, acylacrylonitriles, vinyl sulfinates and vinyl sulfonates of the formula $CH_2$=CX'Y wherein X' is —$SO_2R'$ or —$SO_3R'$ and Y' is —CN, —COOR', —$COCH_3$, —$SO_2R'$ or —$SO_3R'$, and R' is H or hydrocarbyl.

Preferred monomers of formula (I) for use in this invention are alpha-cyanoacrylates. These monomers are known in the art and have the formula

wherein $R^2$ is hydrogen and $R^3$ is a hydrocarbyl or substituted hydrocarbyl group; a group having the formula —$R^4$—O—$R^5$—O—$R^6$, wherein $R^4$ is a 1,2-alkylene group having 2-4 carbon atoms, $R^5$ is an alkylene group having 2-12 carbon atoms, and $R^6$ is an alkyl group having 1-6 carbon atoms; or a group having the formula

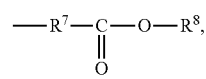

wherein $R^7$ is

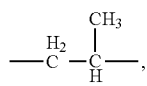

or —$[C(CH_3)_2]_n$— wherein n is 1-10, preferably 1-8 carbon atoms and $R^8$ is an organic moiety.

Examples of suitable hydrocarbyl and substituted hydrocarbyl groups include straight chain or branched chain alkyl groups having 1-16 carbon atoms; straight chain or branched chain $C_1$-$C_{16}$ alkyl groups substituted with an acyloxy group, a haloalkyl group, an alkoxy group, a halogen atom, a cyano group, or a haloalkyl group; straight chain or branched chain alkenyl groups having 2 to 16 carbon atoms; straight chain or branched chain alkynyl groups having 2 to 12 carbon atoms; cycloalkyl groups; aralkyl groups; alkylaryl groups; and aryl groups.

The organic moiety $R^8$ may be substituted or unsubstituted and may be straight chain, branched or cyclic, saturated, unsaturated or aromatic. Examples of such organic moieties include $C_1$-$C_8$ alkyl moieties, $C_2$-$C_8$ alkenyl moieties, $C_2$-$C_8$ alkynyl moieties, $C_3$-$C_{12}$ cycloaliphatic moieties, aryl moieties such as phenyl and substituted phenyl and aralkyl moieties such as benzyl, methylbenzyl and phenylethyl. Other organic moieties include substituted hydrocarbon moieties, such as halo (e.g., chloro-, fluoro- and bromo-substituted hydrocarbons) and oxy- (e.g., alkoxy substituted hydrocarbons) substituted hydrocarbon moieties. Preferred organic radicals are alkyl, alkenyl and alkynyl moieties having from 1 to about 8 carbon atoms, and halo-substituted derivatives thereof. Particularly preferred are alkyl moieties of 4 to 8 carbon atoms.

In the cyanoacrylate monomer of formula (II), $R^3$ is preferably an alkyl group having 1-10 carbon atoms or a group having the formula -$AOR^9$, wherein A is a divalent straight or branched chain alkylene or oxyalkylene moiety having 2-8 carbon atoms, and $R^9$ is a straight or branched alkyl moiety having 1-8 carbon atoms.

Examples of groups represented by the formula -$AOR^9$ include 1-methoxy-2-propyl, 2-butoxy ethyl, isopropoxy ethyl, 2-methoxy ethyl, and 2-ethoxy ethyl.

The preferred alpha-cyanoacrylate monomers used in this invention are 2-octyl cyanoacrylate, n-octyl cyanoacrylate, dodecyl cyanoacrylate, 2-ethylhexyl cyanoacrylate, butyl cyanoacrylate, methyl cyanoacrylate, 3-methoxybutyl cyanoacrylate, 2-butoxyethyl cyanoacrylate, 2-isopropoxyethyl cyanoacrylate, or 1-methoxy-2-propyl cyanoacrylate. The most preferred alpha-cyanoacrylate monomer for use in accordance with the present invention is 2-octyl cyanoacrylate, which has the formula

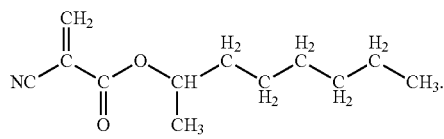

The alpha-cyanoacrylates of formula (II) can be prepared according to methods known in the art. Reference is made, for example, to U.S. Pat. Nos. 2,721,858 and 3,254,111, each of which is hereby incorporated by reference herein. In certain embodiments, the alpha-cyanoacrylates are synthesized based on procedures known in the art. One such process includes, for example, reacting a cyanoacetate with formaldehyde in the presence of a basic condensation catalyst at elevated temperature to give a low molecular weight polymer. A de-polymerization (or cracking) step is followed under high temperature and high vacuum in the presence of acidic and anionic inhibitors, yielding a crude monomer that can be distilled under high temperature and high vacuum in the presence of radical and acidic inhibitors. In preferred embodiments, the distilled 2-cyanoacrylate monomers are then formulated with free radical and acidic inhibitors depending upon their application to provide the necessary stability and other desired physical properties.

The cyanoacrylate component of the compositions according to the present invention can be present from about 10 to about 99.9 percent by weight of the composition, more preferably from about 75 to about 99 percent by weight of the composition, and most preferably from about 90 to about 99 percent by weight of the composition.

The alpha-cyanoacrylate compositions of the present invention also comprise a crown ether compound. The crown ether functions as a polymerization accelerator. Preferred crown ethers for use in accordance with the present invention include, but are not limited to, 15-crown-5, 18-crown-6, dibenzo-18-crown-6, tribenzo-18-crown-6, dicyclohexyl-18-crown-6, benzo-15-crown-5, dibenzo-24-crown-8, dibenzo-30-crown-10, asym-dibenzo-22-crown-6, dimethylsila-11-crown-4, dimethylsila-14-crown-5, dimethylsila-7-crown-6, dibenzo-14-crown-4, dicyclohexyl-24-crown-8, asym-dibenzo-22-crown-6, cyclohexyl-12-crown-4, 1,2-decalyl-15-crown-5, 1,2-naphtho-15-crown-5, 3,4,5-naphthyl-16-crown-5, 1,2-methyl-benzo-18-crown-6, 1,2-methylbenzo-5,6-methylbenzo-18-crown-6, 1,2-t-butyl-18-crown-6, 1,2-vinylbenzo-15-crown-5, 1,2-vinylbenzo-18-crown-6, 1,2-t-butyl-cyclohexyl-18-crown-6, and 1,2-benzo-1,4-benzo-5-oxygen-20-crown-7. 18-crown-6 ethers are particularly preferred.

The crown ether is preferably present in the amount of about 2 to about 3200 ppm by weight of the adhesive composition. In preferred embodiments, the polymerization accelerator is present in the amount of from about 40 to about 1600 ppm, and more preferably from about 100 to about 1000 ppm of the adhesive composition.

The cyanoacrylate monomer compositions according to the present invention can be stabilized with a free radical polymerization inhibitor and an anionic polymerization inhibitor. The preferred free radical stabilizer included in the cyanoacrylate adhesive composition is butylated hydroxyl anisole (BHA), and the preferred anionic vapor phase stabilizer is sulfur dioxide. However, any other suitable free radical stabilizer and anionic vapor phase stabilizer can be used that are known in the art. In embodiments of the present invention where the preferred primary free radical stabilizer is BHA, BHA is typically employed in an amount of from about 200 to about 15000 ppm of the cyanoacrylate compositions, and preferably from about 1000 to about 10000 ppm, and more preferably from about 2000 to about 10000 ppm. In embodiments where the anionic vapor phase stabilizer is $SO_2$, the amount of $SO_2$ that is added to the monomer composition depends on the amount of polymerization accelerator applied such that the higher the concentration of polymerization accelerator, the higher the concentration of $SO_2$. Preferably, the anionic vapor phase stabilizer is added to give a concentration of less than 50 parts per million (ppm).

In certain embodiments, the cyanoacrylate compositions may contain small amounts of a dye (also referred to herein as a "colorant") to enhance the visual detection of the compositions. Colorants such as, for example, derivatives of anthracene and other complex structures may be employed. Suitable dyes include 1-hydroxy-4-[4-methylphenylamino]-9,10 anthracenedione (D&C violet No. 2); 9-(o-carboxyphenyl)-6-hydroxy-2,4,5,7-tetraiodo-3H-xanthen-3-one-, disodium salt, monohydrate (FD&C Red No. 3), disodium salt of 6-hydroxy-5-[(4-sulfophenyl)axo]-2-naphthalene-sulfonic acid (FD&C Yellow No. 6), and 2-(1,3-dihydro-3-oxo-5-sulfo-2H-indole-2-ylidine)-2,3-dihydro-3-oxo-1H-indole-5 sulfonic acid disodium salt (FD&C Blue No. 2).

When employed, the colorant is preferably present in amount of from about 2 to about 50 ppm of the cyanoacrylate composition, more preferably from about 4 to about 40 ppm of the cyanoacrylate composition, and most preferably from about 6 to about 30 ppm of the cyanoacrylate composition.

In preferred embodiments of the present invention, the preferred primary colorant is D&C violet No. 2.

Various other additives such as, for example, thickeners, strength enhancers and polymerization accelerators may be added to vary the viscosity, set time, spreadability, bond strength and degradation rate of the cyanoacrylate compositions of the present invention.

The present invention provides a sterilized cyanoacrylate adhesive composition with a very fast curing speed. This is typically achieved by adding a crown ether cure speed enhancer as described above to the cyanoacrylate adhesive composition before sterilization of the composition. The cure time of cyanoacrylate composition can be improved up to 2-5 times depending upon the amount of the accelerator applied. The cure speed enhancer is soluble in the cyanoacrylate monomer at room temperature. The compositions produced, packaged and sterilized according to the current invention have a much faster cure speed compared to cyanoacrylate adhesive compositions of the prior art.

The reason crown ether was chosen as the preferred cure speed enhancer, or accelerating agent, for cyanoacrylate adhesive is not only due to its excellent activation for curing. Although crown ethers are not known to possess medicinal properties themselves, they may improve drug uptake and transport properties. For example, crown ethers affected the uptake of pirarubicin by drug-resistant cells. (*Biochem. Pharmacol.* 1995, 50, 2069-2076; *Curr. Med. Chem.* 2001, 8, 51-64). The special complexing properties of crown ethers have led to applications in drug delivery systems and as targeting functionalities incorporated in drug derivatives and DNA-binding agents. It was shown in DNA binding studies that the positive charge of cation-crown ether complexes increases the affinity of crown ether linked compounds with the polyanionic phosphate backbone of DNA. Thus, crown ether derivatized drugs may gain an increased interaction with DNA by the formation of cationic complexes with ions that are abundant in cells, such as sodium or potassium. (*Int. J. Pharm.* 1997, 159, 207-213; *Int J. Pharm.* 1998, 172, 33-70; *Bioorg. Med. Chem. Lett.* 1994, 4, 1123-1126).

Preferably, the cyanoacrylate adhesive compositions according to the present invention are stable. As the cure speed of cyanoacrylate adhesive compositions has been dramatically improved herein, the stability of the adhesive is still conserved. Such stability of the adhesive is sustained due to the following treatments: (a) reducing the amount of contaminants and extraneous additives by applying the particulate agent, (b) providing a stable cyanoacrylate adhesive composition by use of the combination of free radical stabilizer and anionic stabilizing agent and (c) further stabilizing the cyanoacrylate adhesive composition by applying more anionic stabilizer. Even with the presence of the cure speed enhancer, the cyanoacrylate adhesive composition does not actually cure until it has been applied to tissue.

The stability of the cyanoacrylate adhesive composition with the cure speed enhancer is confirmed by both real time and accelerated aging test detailed in the Examples below. Both the set time and viscosity data indicate the stability of the inventive cyanoacrylate adhesive composition, also detailed below.

The cyanoacrylate adhesive composition has a viscosity in the range from 2.5 to 70 centipoise, and preferably 5-30 centipoise, as measured with a Brookfield Viscometer at 25° C. Additionally, the viscosity of the composition should be maintained or increased by a controlled and acceptable amount after sterilization.

The cure time of cyanoacrylate adhesives in the absence of the cure speed enhancer is up to 90 seconds depending upon the amount of free radical and anionic stabilizers included. However, the cure speed is dramatically increased after applying the cure speed enhancer to the cyanoacrylate composition. An increase of up to a few seconds can be achieved depending on the amount of the cure speed enhancer applied.

According to embodiments of the present invention, the stability, and thus the shelf-life, of the cyanoacrylate adhesive compositions in the presence of the cure speed enhancer can be maintained during the accelerated aging, the packaging and sterilizing procedures. In preferred embodiments, there is substantially no initiation of polymerization of monomeric liquid adhesive compositions that affects the utility of the monomer caused by the sterilization process.

The accelerated aging test of cyanoacrylate adhesive composition was performed in the oven at 80° C. for a period of 12 days. Based on the calculation, 12 days accelerated aging at 80° C. is equal to 2 years of shelf life, and 1 day of accelerated aging at 80° C. is equal to 60.8 days. Throughout the entire aging procedure, all cyanoacrylate adhesive samples remained fluid consistency and in good color. The stability of the aged cyanoacrylate adhesive samples was confirmed by set time and viscosity test.

The viscosity of the cyanoacrylate adhesive composition with the cure speed enhancer increased as the accelerated aging proceeded but the viscosity of the aged sample after day 12 was in the acceptable range. As an example, the average viscosity of cyanoacrylate adhesive composition in the presence of the cure speed enhancer at accelerated aging day 0, day 3, day 6, day 9, and day 12 was 4.29, 5.72, 10.6, 25.5, and 53.1 centipoise, respectively.

The cure time of the cyanoacrylate adhesive composition with cure speed enhancer varied a little after the 12 days aging at 80° C. However, the cure time of the cyanoacrylate adhesive composition in the absence of the cure speed enhancer might be dropped a lot during the accelerated aging process. For example, the average set time of one adhesive made from 2-octyl cyanoacrylate was increased from 40 seconds before the accelerated aging to 65 and 112 seconds at day 6 and day 12, respectively.

Vinyl pyrrolidone polymers and copolymers can be applied to reduce the amount of contaminants and extraneous additives in the resulting adhesives from the cyanoacrylate adhesive formulation. These particulate agents are combined with the monomer adhesive in mutual contact until the adhesive is destabilized, whereupon the adhesive becomes isolated from the destabilizing agent by various means such as to effect isolation of the adhesive from the destabilizing component. It is only a requisite that enough excess stabilizer is left behind so as to provide the desirable speed of cure.

The purity of cyanoacrylate adhesive compositions was checked by GC-MS. More than 99% of the adhesive composition is 2-octyl cyanoacrylate. No plasticizer or thixotropic agent is incorporated in the inventive cyanoacrylate adhesive composition.

The cyanoacrylate adhesive compositions are sterilized. This is one novel aspect of the invention, as prior cyanoacrylate compositions with accelerators were not sterilized for medical use. The sterilization can be accomplished by common techniques, and is preferably accomplished by methods including, but not limited to, chemical, physical, and irradiation methods. Examples of chemical methods include, but are not limited to, exposure to ethylene oxide. Examples of irradiation methods include, but are not limited to, gamma irradiation, electron beam irradiation, and microwave irradiation. Preferred methods are chemical sterilization and electron beam sterilization. Also, the cyanoacrylate compositions can be sterilized with ultraviolet (UV) radiation. Further, upon sterilization with any of these methods, the cyanoacrylate adhesive compositions are not cured. In other words, curing does not occur until application to tissue.

The sterility of the cyanoacrylate monomer composition with the cure speed enhancer was analyzed by Bacteriostasis and Fungistasis tests. The test sample consisted of the sample with a puncture created to allow the liquid inside of the sample to mix with the test media. All were immersed into 500 ml of Soybean Casein Digest Medium (SCDM). The test microorganism such as *Bacillus subtilis, Candida albicans*, and *Aspergillus niger*, at less than 100 colony forming units, was inoculated into each of the test sample containers and into a positive control container of the same medium. After inoculation, the test sample and positive control container were incubated at 20-25 DC for a five day maximum incubation period. The growth of *Bacillus subtilis, Candida albicans*, and *Aspergillus niger* was observed for the inventive cyanoacrylate adhesive before the sterilization, while the inventive adhesives after sterilization exert a gross fungistatic effect on *Bacillus subtilis, Candida albicans*, and *Aspergillus niger*.

In vivo biomechanical evaluation was performed using the rat linear incision wound model in order to assess and evaluate the efficacy of the cyanoacrylate composition with the cure speed enhancer as a new topical surgical tissue adhesive for the application of incisional wound closure. For direct comparison, the commercially available product Dermabond® topical skin adhesive was also evaluated. The male Sprague-Dawley rat was chosen as the animal model and this animal model has been used extensively for incisional wound strength studies, which has been well documented in the literature. All study animals were acclimatized to their designated housing for approximately 7 days prior to the day of treatment. Prior to surgery, final selection of the animals was based on a visual appraisal of good clinical condition, and body weight specifications.

TABLE 1

Biomechanical wound strength results for the cyanoacrylate adhesive of the present invention and Dermabond ® topical skin adhesive.
Raw Data

| Date | Study Time Point | Animal | Study Group | Group Description | Side [L = Left/R = Right] |
|---|---|---|---|---|---|
| May 8, 2006 | acute | 1 | A | DERMABOND ® High Viscosity | L |
| May 8, 2006 | acute | 2 | A | DERMABOND ® High Viscosity | R |
| May 8, 2006 | acute | 3 | A | DERMABOND ® High Viscosity | L |
| May 8, 2006 | acute | 4 | A | DERMABOND ® High Viscosity | R |
| May 8, 2006 | acute | 5 | A | DERMABOND ® High Viscosity | L |
| May 8, 2006 | acute | 6 | A | DERMABOND ® High Viscosity | R |
| May 8, 2006 | acute | 7 | A | DERMABOND ® High Viscosity | L |
| May 8, 2006 | acute | 8 | A | DERMABOND ® High Viscosity | R |
| May 8, 2006 | acute | 9 | A | DERMABOND ® High Viscosity | L |
| May 8, 2006 | acute | 10 | A | DERMABOND ® High Viscosity | R |
| May 8, 2006 | acute | 11 | A | DERMABOND ® High Viscosity | L |
| May 8, 2006 | acute | 12 | A | DERMABOND ® High Viscosity | R |
| May 8, 2006 | acute | 13 | A | DERMABOND ® High Viscosity | L |
| May 8, 2006 | acute | 14 | A | DERMABOND ® High Viscosity | R |
| May 8, 2006 | acute | 1 | B | Inventive Adhesive | R |
| May 8, 2006 | acute | 2 | B | Inventive Adhesive | L |
| May 8, 2006 | acute | 3 | B | Inventive Adhesive | R |
| May 8, 2006 | acute | 4 | B | Inventive Adhesive | L |
| May 8, 2006 | acute | 5 | B | Inventive Adhesive | R |
| May 8, 2006 | acute | 6 | B | Inventive Adhesive | L |
| May 8, 2006 | acute | 7 | B | Inventive Adhesive | R |
| May 8, 2006 | acute | 8 | B | Inventive Adhesive | L |
| May 8, 2006 | acute | 9 | B | Inventive Adhesive | R |
| May 8, 2006 | acute | 10 | B | Inventive Adhesive | L |
| May 8, 2006 | acute | 11 | B | Inventive Adhesive | R |
| May 8, 2006 | acute | 12 | B | Inventive Adhesive | L |
| May 8, 2006 | acute | 13 | B | Inventive Adhesive | R |
| May 8, 2006 | acute | 14 | B | Inventive Adhesive | L |

| Date | Wound Size | Termination Weight (g) | Ultimate Pressure (mmHg) | Comments |
|---|---|---|---|---|
| May 8, 2006 | 1 | 275 | 271 | |
| May 8, 2006 | 1 | 297 | 230 | |
| May 8, 2006 | 1 | 286 | 291 | |
| May 8, 2006 | 1 | 285 | 163 | |
| May 8, 2006 | 1 | 290 | 226 | |
| May 8, 2006 | 1 | 297 | 169 | |

TABLE 1-continued

Biomechanical wound strength results for the cyanoacrylate adhesive of the present invention and Dermabond ® topical skin adhesive.
Raw Data

| | | | |
|---|---|---|---|
| May 8, 2006 | 1 | 280 | 162 |
| May 8, 2006 | 1 | 277 | 200 |
| May 8, 2006 | 1 | 294 | 161 |
| May 8, 2006 | 1 | 284 | 276 |
| May 8, 2006 | 1 | 282 | 320 |
| May 8, 2006 | 1 | 287 | 105 |
| May 8, 2006 | 1 | 280 | 326 |
| May 8, 2006 | 1 | 205 | 372 |
| | Mean | 255.5 | 240.0 |
| | St. Dev. | 5.3 | 70.1 |
| May 8, 2006 | 1 | 275 | 210 |
| May 8, 2006 | 1 | 297 | 220 |
| May 8, 2006 | 1 | 286 | 164 |
| May 8, 2006 | 1 | 285 | 215 |
| May 8, 2006 | 1 | 290 | 119 |
| May 8, 2006 | 1 | 287 | 274 |
| May 8, 2006 | 1 | 280 | 314 |
| May 8, 2006 | 1 | 277 | 243 |
| May 8, 2006 | 1 | 294 | 251 |
| May 8, 2006 | 1 | 284 | 235 |
| May 8, 2006 | 1 | 282 | 291 |
| May 8, 2006 | 1 | 287 | 261 |
| May 8, 2006 | 1 | 280 | 285 |
| May 8, 2006 | 1 | 292 | 175 |
| | Mean | 255.5 | 231.7 |
| | St. Dev. | 6.3 | 52.5 |
| ANOVA (p = 0.05) | | | p-value 0.736201604 |

The animals were anesthetized, placed on a surgical table with a water-heating pad, and prepped with Betadine surgical skin prep and 70% alcohol solution. To control incision length and location, a template and surgical skin-marking pen were used to mark two symmetric 0.75-inch linear incisions over each dorsolateral flank area. All animals underwent the same surgical procedure. All incisions were made by the same surgeon and extend through the skin, subcutaneous tissue and panniculus carnosus. The incisional wounds were then biomechanically tested for incisional wound strength.

A BTC disposable acrylic test ring (ID 2.5 cm) was placed around the wound and secured to the skin using cyanoacrylate adhesive with the cure speed enhancer or commercially available Dermabond® topical skin adhesive. A small amount of perfluorinated grease was applied to the top of the ring interface to assure a tight vacuum seal. The BTC-2000™ test chamber was integrated with the test ring until the chamber and ring were securely interconnected. The test chamber was held by hand comfortably to assure that no positive force was being exerted on the wound. A constant negative pressure was applied to the wound at a rate of 10 mmHg/second, producing a multi-axial stress on the wound. A displacement laser captured displacement of wound margins.

Based on the wound strength raw data presented in Table 1, the average ultimate pressure applied in wound site for the inventive cyanoacrylate adhesive and the commercial Dermabond® topical skin adhesive was in the same level, indicating the cyanoacrylate with the cure speed enhancer possesses a bond strength strong enough to be used for wound closure as a medical product.

In vitro cytotoxicity of the cyanoacrylate adhesive with the cure speed enhancer was evaluated. For comparison, the commercially available Dermabond® topical skin adhesive was also evaluated. A 2 cm$^2$ sterile disc of filter paper was saturated with 2-octylcyanoacrylate adhesive composition with the cure speed enhancer prior to dosing. L 929 mammalian fibroblast cell, seeded at a density of about 100,000 cells per mL at 7 mL per 60×15 mm plate, were allowed to propagate in serum supplemented minimum essential medium in a single test plate until greater than 80% confluence was observed. Growth generally requires about 48 to 72 hours in a humidified carbon dioxide incubator at 37±1° C. When the cell culture reached confluence, the growth media was removed aseptically and triplicate plates were refilled with serum supplemented culture media containing not more than 2% agar overlay. The flat surface of the cyanoacrylate adhesive sample, positive and negative controls, and media control was then placed in contact with solidified agar surface. The test plates were then returned to the incubator for 24 hours. At the end of the additional incubation, the plates were individually observed under an inverted light microscope for signs of cell toxicity. The test results (Table 2) indicated that only minimal cytotoxicity was observed for the cyanoacrylate adhesive with the cure speed enhancer, while minimal to mild cytotoxicity was observed for the control Dermabond® topical skin adhesive.

TABLE 2

Results of test for in vitro cytotoxicity.

| Test article | Evaluation of cytotoxicity |
|---|---|
| The inventive adhesive | ±, ±, ± |
| Dermabond ® topical skin adhesive | ±, ±, 1 |
| USP HDPE RS (Negative control) | 0, 0, 0 |
| USP Bioreaction RS (Positive control) | 2, 2, 2 |
| Media Control (MEM) | 0, 0, 0 |

| Ratings | | |
|---|---|---|
| 0 | Noncytotoxic | No detectable zone around or under specimen |
| ± | Slight cytotoxic | Some malformed or degenerated cells under specimen |
| 1 | Mildly cytotoxic | Zone limited to area under specimen |

TABLE 2-continued

Results of test for in vitro cytotoxicity.

| | | |
|---|---|---|
| 2 | Moderate cytotoxic | Zone extends 0.5 to 1.0 cm beyond specimen |
| 3 | Severely cytotoxic | Zone extends greater than 1.0 cm beyond specimen |

The above results of the in vivo biomechanical evaluation using the rat linear incision wound model revealed that the inventive cyanoacrylate adhesive has comparable bond strength as the commercial Dermabond® product. In addition, in vitro cytotoxicity provided additional evidence that the cyanoacrylate adhesive is more suitable for medical use. The inventive cyanoacrylate adhesive exhibits only minimally cytotoxicity, while minimally to mild cytotoxicity was observed for the control Dermabond® product. Therefore, the cyanoacrylate adhesive of the present invention has advantages over the prior art.

The cyanoacrylate compositions of the present invention are especially suitable for use in medical applications. In use, the cyanoacrylate adhesive composition is applied to the desired tissue area as a liquid which then polymerizes upon contact with tissue. The cure speed enhancer allows for quick polymerization and setting of the cyanoacrylate adhesive composition, i.e., quick curing. The polymerized patch of cyanoacrylate adhesive allows the tissue to heal properly. Over time, water is drawn into the adhesive, causing it to degrade. The components of the adhesive then are cleared from the body.

A surprising advantage of the cyanoacrylate adhesive compositions according to the present invention is that the adhesives exhibit a desirable permeability or breathability. The cyanoacrylate adhesive films according to the present invention typically exhibit a moisture vapor transmission rate of at least 950 $g/m^2/day$ when measured according to ASTM D-6701 using a Mocon Permatran-W101 water vapor permeability instrument. Preferably, the cyanoacrylate adhesive films exhibit a moisture vapor transmission rate of from about 950 to about 3000 $g/m^2/day$, more preferably from about 1000 to about 2500 $g/m^2/day$, still more preferably from about 1500 to about 2200 $g/m^2/day$, still more preferably from about 1800 to about 2100 $g/m^2/day$, and most preferably from about 1900 to about 2100 $g/m^2/day$. Such transmission rates are important in surgical applications because if the moisture vapor transmission rate is too low, a large quantity of exudates are prone to be trapped next to the wound at a significant fluid pressure, which usually results in extensive skin macerations. On the other hand, if the moisture vapor transmission rate of the adhesive film is too high, the exudates moisture would be removed so fast as to desiccate the wound. Therefore, using a surgical adhesive with a desirable permeability rate is highly important in maintaining an optimal microenvironment at wound closing site.

The cyanoacrylate compositions of the present invention also provide a cyanoacrylate-based adhesive that strongly bonds to human skin while maintaining the desired high moisture vapor transmission rate for a better wound healing microenvironment. The strong bonding strength of the cyanoacrylate adhesive compositions with the polymerization accelerator was confirmed by following ASTM method to measure the mechanical strengths, included but not limited to, T-peel tensile strength, lap-shear tensile strength, tensile strength in tension, and wound closure tensile strength.

Lap-shear tensile strength of the cyanoacrylate adhesive compositions including a polymerization accelerator with a desired high MVTR was measured in accordance with ASTM F2255-05. The lap shear tensile strength is the force required to break two overlapped pieces of pig skin adhered by the disclosed cyanoacrylate adhesive composition, which were attached onto two steel substrates. The cyanoacrylate adhesive composition including a polymerization accelerator has a lap shear tensile strength of from about 12 to about 18 $lbs/in^2$.

T-peel strength is the force required to yield the separation of two flexible adherends bonded by the disclosed cyanoacrylate adhesives, which is measured according to ASTM F2256-05. The cyanoacrylate adhesive disclosed herein provides a T-peel tensile strength of from about 34 to about 48 lbs.

Tensile strength in tension of the cyanoacrylate adhesive including the polymerization accelerator with a desired high permeability was measured in accordance with ASTM F2258-05. The tensile strength in tension is the force required to break two pieces of pig skins adhered by the inventive adhesive, which are attached onto the stamp-shape steel substrate. The cyanoacrylate adhesive composition has a tensile strength in tension of from about 12 to about 16 $lbs/in^2$.

Wound closure strength of the cyanoacrylate adhesive including the polymerization accelerator with a desired permeability was evaluated based on ASTM F2458-05. Wound closure strength is the force required to break two pieces of pig skin connected by the inventive adhesive mimicking the wound closure of the incision. The inventive cyanoacrylate adhesive composition has a wound closure strength of from about 1.5 to about 4 $lbs/in^2$, and preferably from about 2 to about 4 $lbs/in^2$.

The present invention further provides for a kit for applying the cyanoacrylate adhesive composition of the present invention, including an applicator containing therein an effective amount of the cyanoacrylate composition. The applicator can be any suitable applicator such as, but not limited to, Q-tips, a swab, or an applicator tip on a container with the cyanoacrylate composition therein. The kit can further contain directions for application. When the present invention is used with other therapeutics, separate containers can be provided for the cyanoacrylate composition and the therapeutic for application.

Individual applicators can be packaged separately to maintain sterile conditions. For example, each applicator can be packaged in plastic or any other suitable enclosing material. Multiple applicators can then be packaged in a box for shipping.

The compound of the present invention is administered and dosed in accordance with good medical practice, taking into account the clinical condition of the individual patient, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including but not limited to improved survival rate or more rapid recovery, or improvement or elimination of symptoms and other indicators as are selected as appropriate measures by those skilled in the art.

In the method of the present invention, the compound of the present invention can be administered in various ways. It should be noted that it can be administered as the compound and can be administered alone or as an active ingredient in combination with pharmaceutically acceptable carriers, diluents, adjuvants and vehicles. The compounds can be administered in any suitable way. Implants of the compounds are also useful. The patients being treated are warm-blooded animals and, in particular, mammals including human beings. The pharmaceutically acceptable carriers, diluents, adjuvants and vehicles as well as implant carriers generally refer to inert, nontoxic solid or liquid fillers, diluents or encapsulating material not reacting with the active ingredients of the invention.

The doses can be single doses or multiple doses over a period of several days. The treatment generally has a length proportional to the length of the disease process and drug effectiveness and the patient species being treated.

When administering the compound of the present invention parenterally, it will generally be formulated in a unit dosage injectable form (solution, suspension, emulsion). The pharmaceutical formulations suitable for injection include sterile aqueous solutions or dispersions and sterile powders for reconstitution into sterile injectable solutions or dispersions. The carrier can be a solvent or dispersing medium containing, for example, water, ethanol, polyol (for example, glycerol, propylene glycol, liquid polyethylene glycol, and the like), suitable mixtures thereof, and vegetable oils.

Proper fluidity can be maintained, for example, by the use of a coating such as lecithin, by the maintenance of the required particle size in the case of dispersion and by the use of surfactants. Nonaqueous vehicles such a cottonseed oil, sesame oil, olive oil, soybean oil, corn oil, sunflower oil, or peanut oil and esters, such as isopropyl myristate, may also be used as solvent systems for compound compositions. Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the compounds.

Sterile injectable solutions can be prepared by incorporating the compounds utilized in practicing the present invention in the required amount of the appropriate solvent with various of the other ingredients, as desired.

A pharmacological formulation of the present invention can be administered to the patient in an injectable formulation containing any compatible carrier, such as various vehicles, adjuvants, additives, and diluents; or the compounds utilized in the present invention can be administered parenterally to the patient in the form of slow-release subcutaneous implants or targeted delivery systems such as monoclonal antibodies, vectored delivery, iontophoretic, polymer matrices, liposomes, and microspheres. Examples of delivery systems useful in the present invention include those disclosed in U.S. Pat. Nos. 5,225,182; 5,169,383; 5,167,616; 4,959,217; 4,925,678; 4,487,603; 4,486,194; 4,447,233; 4,447,224; 4,439,196; and 4,475,196. Many other such implants, delivery systems, and modules are well known to those skilled in the art.

Additional objects, advantages, and novel features of this invention will become apparent to those skilled in the art upon examination of the following examples of the invention. The examples are included to more clearly demonstrate the overall nature of the invention and, thus, are illustrative and not restrictive of the invention.

EXAMPLES

Example 1

197.4 g of 2-octyl cyanoacrylate was mixed with 0.20 g of poly vinyl pyrrolidone (PVP) under vacuum for 2 hours and solid powder was removed by filtration. The resulting solution was mixed with certain amounts of stabilizer, BHA, and colorant, D & C Violet under vacuum for a minimum of 0.5 hour. A sulfur dioxide solution in 2-octyl cyanoacrylate was charged into the solution to further stabilize the cyanoacrylate composition. The resulting purple solution was then filtered with a micrometer filter to yield the activated 2-octyl cyanoacrylate adhesive composition.

Example 2

27 pounds of the activated 2-octyl cyanoacrylate was charged into stainless steel container equipped with the mechanical agitator. 0.12 g of $SO_2$ solution (5.8%) in 2-octyl cyanoacrylate was added to the container and stirred for a minimum of 0.5 hour. 3.3 g of 18-crown-6 was dissolved in 30 mL of 2-octyl cyanoacrylate in microwave, which was added to the bulk solution of 2-octyl cyanoacrylate in the stainless steel container and stirred for a minimum of 0.5 hour. After the filtration, the resulting cyanoacrylate adhesive composition was subjected to viscosity, set time, bond strength and accelerated aging tests (see Table 3). The bond strength measured for the samples at day 0 and day 12 are 773.9, and 723.2 lbs/inch$^2$, respectively.

TABLE 3

Set time and viscosity results of examples 2 and 3.

| | Aging condition | Day 0 | | Day 6 | | Day 9 | | Day 12 | |
|---|---|---|---|---|---|---|---|---|---|
| | | Set time (s) | Viscosity (cps) | Set time (s) | Viscosity (cps) | Set time (s) | Viscosity (cps) | Set time (s) | Viscosity (cps) |
| Example 2 | 12 days 80° C. | 22 | 4.35 | 20 | 4.56 | 18 | 4.78 | 28 | 5.65 |
| Example 3 | 12 days 80° C. | 35 | 5.43 | 33 | 4.99 | 24 | 6.30 | 28 | 6.52 |

Example 3

18 pounds of the activated 2-octyl cyanoacrylate was charged into stainless steel container equipped with the mechanical agitator. 0.078 g of $SO_2$ solution (5.8%) in 2-octyl cyanoacrylate was added to the container and stirred for a minimum of 0.5 hour. 1.5 g of 18-crown-6 was dissolved in 30 mL of 2-octyl cyanoacrylate in microwave, which was added to the bulk solution of 2-octyl cyanoacrylate in the stainless steel container and stirred for a minimum of 0.5 hour. After the filtration, the resulting cyanoacrylate adhesive composition was subjected to viscosity, set time, bond strength and accelerated aging tests (see Table 3). The bond strength measured for the samples at day 0 and day 12 are 714.5, and 703.1 lbs/inch$^2$, respectively.

Example 4

864.4 g of the activated 2-octyl cyanoacrylate was put into 1 L of opaque polyethylene bottle. 0.142 g of $SO_2$ solution (5.8%) in 2-octyl cyanoacrylate was added to the container and stirred for a minimum of 1 hour.

Example 5

To a polyethylene bottle, 30.8 g of 2-octyl cyanoacrylate from Example 4 was mixed with 98.6 mg of 18-crown-6 and stirred at room temperature for 2 hours. The sample was subjected to the accelerated aging test at 80° C. The average set time for the samples at day 0, day 6, and day 12 are 6.7, 7.3, and 9.4 s, respectively. The average viscosity for the samples at day 0, day 6, and day 12 are 3.27, 2.86, and 28.8 cps, respectively.

Example 6

To a polyethylene bottle, 30.1 g of 2-octyl cyanoacrylate from Example 4 was mixed with 72.4 mg of 18-crown-6 and stirred at room temperature for 2 hours. The sample was subjected to the accelerated aging test at 80° C. The average set time for the samples at day 0, day 6, and day 12 are 8.3, 9, and 14 s, respectively. The average viscosity for the samples at day 0, day 6, and day 12 are 2.86, 2.86, and 24.3 cps, respectively.

Example 7

To a polyethylene bottle, 30.9 g of 2-octyl cyanoacrylate from Example 4 was mixed with 30.9 mg of 18-crown-6 and stirred at room temperature for 2 hours. The sample was subjected to the accelerated aging test at 80° C. The average set time for the samples at day 0, day 6, and day 12 are 14.7, 14.7, and 19.3 seconds, respectively. The average viscosity for the samples at day 0, day 6, and day 12 are 3.06, 3.06, and 20.4 cps, respectively.

Example 8

To a polyethylene bottle, 30.5 g of 2-octyl cyanoacrylate from Example 4 was mixed with 21.4 mg of 18-crown-6 and stirred at room temperature for 2 hours.

Example 9

In a polyethylene bottle, 4.4 g of 2-octyl cyanoacrylate composition from example 8 was diluted to 30.8 g by 2-octyl cyanoacrylate composition from Example 4 and stirred at room temperature for 2 hours. The sample was subjected to the accelerated aging test at 80° C. The average set time for the samples at day 0, day 6, and day 12 are 33, 35.3, and 39 seconds, respectively. The average viscosity for the samples at day 0, day 6, and day 12 are 2.65, 2.65, and 9.19 cps, respectively.

Example 10

In a polyethylene bottle, 0.616 g of 2-octyl cyanoacrylate composition from Example 9 was diluted to 30.8 g by 2-octyl cyanoacrylate composition from example 4 and stirred at room temperature for 2 hours. The sample was subjected to the accelerated aging test at 80° C. The average set time for the samples at day 0, day 6, and day 12 are 70.3, 73.7, and 75 seconds, respectively. The average viscosity for the samples at day 0, day 6, and day 12 are 2.87, 2.65, and 3.06 cps, respectively.

Example 11

473.4 g of the activated 2-octyl cyanoacrylate was put into 1 L of opaque polyethylene bottle. 4.5 mg of $SO_2$ solution (5.8%) in 2-octyl cyanoacrylate was added to the container and stirred for a minimum of 1 hour.

Example 12

To a polyethylene bottle, 30.1 g of 2-octyl cyanoacrylate from Example 11 was mixed with 96.5 mg of 18-crown-6 and stirred at room temperature for 2 hours. The sample was subjected to the accelerated aging test at 80° C. The average set time for the samples at day 0, day 6, and day 12 are 6.7, 6.3, and 7.7 seconds, respectively. The average viscosity for the samples at day 0, day 6, and day 12 are 2.86, 3.47, and 11.4 cps, respectively.

Example 13

To a polyethylene bottle, 30.1 g of 2-octyl cyanoacrylate from Example 11 was mixed with 48.3 mg of 18-crown-6 and stirred at room temperature for 2 hours. The sample was subjected to the accelerated aging test at 80° C. The average set time for the samples at day 0, day 6, and day 12 are 10, 9.7, and 11 seconds, respectively. The average viscosity for the samples at day 0, day 6, and day 12 are 3.06, 3.27, and 7.33 cps, respectively.

Example 14

To a polyethylene bottle, 29.9 g of 2-octyl cyanoacrylate from Example 11 was mixed with 29.9 mg of 18-crown-6 and stirred at room temperature for 2 hours. The sample was subjected to the accelerated aging test at 80° C. The average set time for the samples at day 0, day 6, and day 12 are 12.7, 11, and 12.3 seconds, respectively. The average viscosity for the samples at day 0, day 6, and day 12 are 2.65, 3.24, and 3.68 cps, respectively.

Example 15

To a polyethylene bottle, 30.0 g of 2-octyl cyanoacrylate from Example 11 was mixed with 8.10 mg of 18-crown-6 and stirred at room temperature for 2 hours. The sample was subjected to the accelerated aging test at 80° C. The average set time for the samples at day 0, day 6, and day 12 are 17, 15, and 17.3 seconds, respectively. The average viscosity for the samples at day 0, day 6 and day 12 are 2.87, 2.65, and 3.27 cps, respectively.

Example 16

To a polyethylene bottle, 19.6 g of 2-octyl cyanoacrylate from Example 11 was mixed with 9.9 mg of 18-crown-6 and stirred at room temperature for 2 hours.

Example 17

In a polyethylene bottle, 2.4 g of 2-octyl cyanoacrylate composition from Example 16 was diluted to 30 g by 2-octyl cyanoacrylate composition from Example 11 and stirred at room temperature for 2 hours. The sample was subjected to the accelerated aging test at 80° C. The average set time for the samples at day 0, day 6, and day 12 are 42.3, 55.3, and 47 seconds, respectively. The average viscosity for the samples at day 0, day 6, and day 12 are 2.87, 3.27, and 2.65 cps, respectively.

Example 18

In a polyethylene bottle, 0.59 g of 2-octyl cyanoacrylate composition from Example 16 was diluted to 30 g by 2-Octyl cyanoacrylate composition from Example 11 and stirred at room temperature for 2 hours. The sample was subjected to the accelerated aging test at 80° C. The average set time for the samples at day 0, day 6, and day 12 are 53.7, 67, and 61.7 seconds, respectively. The average viscosity for the samples at day 0, day 6, and day 12 are 3.06, 2.87, and 3.47 cps, respectively.

Example 19

33.4 pounds of the activated 2-octyl cyanoacrylate was charged into stainless steel container equipped with the mechanical agitator. 0.144 g of $SO_2$ solution (5.8%) in 2-octyl cyanoacrylate was added to the container and stirred for a minimum of 0.5 hour. 4.06 g of 18-crown-6 was added to the bulk solution of 2-octyl cyanoacrylate in the stainless steel container and stirred for a minimum of 0.5 hour. After the filtration, the resulting cyanoacrylate adhesive composition was subjected to viscosity, set time, bond strength and accelerated aging tests.

Example 20

To a polyethylene bottle, 30.8 g of 2-octyl cyanoacrylate composition from Example 19 was mixed with 90.5 mg of 18-crown-6 and stirred at room temperature for 2 hours. The sample was subjected to the accelerated aging test at 80° C. The average set time for the samples at day 0, day 6, and day 12 are 8.67, 11, and 11.3 seconds, respectively. The average viscosity for the samples at day 0, day 6, and day 12 are 3.06, 2.86, and 55.2 cps, respectively.

Example 21

To a polyethylene bottle, 30.8 g of 2-octyl cyanoacrylate composition from Example 19 was mixed with 41.3 mg of 18-crown-6 and stirred at room temperature for 2 hours. The sample was subjected to the accelerated aging test at 80° C. The average set time for the samples at day 0, day 6, and day 12 are 17, 24.3, and 22 seconds, respectively. The average viscosity for the samples at day 0, day 61 and day 12 are 2.45, 2.65, and 23.8 cps, respectively.

Example 22

The shelf-life study for the inventive adhesive (2-octyl cyanoacrylate with 18-crown-6) was investigated by real-time aging at room temperature. The real-time shelf-life study is verified on the increments of Day 0, Month 1, 3, 6, 9, 12 and 24. The stability was assessed by viscosity and set time. Table 4 shows the average viscosity and set time of the inventive adhesive at different time of the shelf life study.

TABLE 4

|  | Viscosity | Set-Time |
|---|---|---|
| Initial | 3.47 cps | 15 sec |
| Month 1 | 4.29 cps | 16 sec |
| Month 3 | 4.29 cps | 16 sec |
| Month 6 | 3.88 cps | 19 sec |
| Month 9 | 4.70 cps | 16 sec |
| Month 12 | 6.74 cps | 21 sec |
| Month 24 | 6.70 cps | 45.5 sec |

Example 23

Heat of polymerization of 2-octyl cyanoacrylate adhesives with cure speed enhancer was measured with DSC. Samples were transferred to an aluminum DSC pan via disposable pipette from a freshly opened applicator. Each sample was heated from 30° C. to 300° C. at a rate of 10° C./min in an atmosphere of nitrogen flowing at a rate of 20 cc/min. In each product there appears to be a two stage polymerization which cannot be accurately separated using a temperature ramp of 10° C. per minute. The average heat of polymerization is 225 J/g.

Example 24

Permeability

Permeability of the inventive surgical adhesive (2-Octyl cyanoacrylate with 18-crown-6 polymerization accelerator) was determined by measuring moisture vapor transmission rate (MVTR) using the PERMATRAN-W Model 101K in accordance with ASTM D06701. The adhesive sample was applied and cured on collagen film with a dimension of 2"×2". The sample film was then mounted in one of the test cells. The test cells are divided into two chambers. The lower chamber is filled with nitrogen and the upper chamber with water vapor. A cell calibration, consisting of a measurement of the equilibrated water vapor transmission through a guard film is performed. The adhesive film to be tested is then mounted and the corresponding transmission rate is determined by measuring the reduction in the amount of water vapor present in the lower chamber. As a comparison, the MVTR of Dermabond® topical skin adhesive was also measured. In addition, the MVTR of collagen film is measured as a control. The results of MVTR are summarized in Table 5.

TABLE 5

Moisture Vapor Transmission Rate of the inventive adhesive, Dermabond ® topical skin adhesive and collagen film

| | MVTR (g/m$^2$/day) | | |
|---|---|---|---|
| | Replicate 1 | Replicate 2 | Average |
| Example 24 adhesive | 2260 | 2100 | 2180 |
| Dermabond ® topical skin adhesive | 901 | 935 | 918 |
| Collagen film | 11,100 | 9640 | 10,370 |

Example 25

Sample Preparation and Conditions for Tensile Strength Test

Tissue Preparation:
1. Tissue substrate materials (porcine skin) were kept moist at all times with phosphate buffered saline (PBS).
2. The tissue substrate was cut into suitable dimensions.
3. The back side of the tissue was glued to the test fixture using Super glue. Care was taken to ensure that the substrate was aligned square with the sides of the test fixtures and to not extend past the end of the fixture.
4. Wrap the tissue with gauze soaked in PBS, place the fixtures in a plastic bag, and place them in a water bath at 37° C.

Preparation of the Adhesive Bond:
1. Removed the test fixtures from the plastic bag and patted the surface of porcine skin dry with fresh gauze.
2. Applied sufficient adhesive to uniformly coat the overlap area without significant overflow.
3. Bonded the two sides of the test fixture together, taking care to keep the fixture aligned and to maintain the prescribed overlap.
4. Applied suitable force to the bond area until the adhesive set.
5. Covered the bonded tissue with gauze soaked in PBS and placed the sample in a plastic bag, and returned it to the water bath at 37° C.

Procedure for Sample Conditioning and Test:
1. Conditioned the test specimens for 1 hour and 15 minutes. Recommended conditions for Tissue adhesives intended for internal applications are 37±1° C. in phosphate buffered saline. For adhesives intended for external topical use, recommended conditions are 30±1° C. and 50±5% relative humidity. For quality control testing, the recommended conditions are 23±2° C. and 50±5% relative humidity.
2. After conditioning, specimens were stabilized at the test temperature for 15 min before testing if the test temperature is different from the conditioning temperature. Tissue samples were kept moist throughout the process to prevent shrinkage due to drying. For comparative testing the test conditions should be 23±2° C. and 50±5% relative humidity.
3. Placed the test specimens in the grips of the testing machine so that the applied load coincides with the long axis of the specimen. Load the specimen to failure at a constant cross-head speed.
4. Recorded the load at failure (maximum load sustained) and the type of failure (percentage cohesive, adhesive, or substrate failure based on observation of the bond area). Failure Rate—Tissue substrates tend to give higher variances and may require more samples to attain a reasonable estimate of the mean strength.

Example 26

Tensile Strength in Tension

This test method is intended to provide a means for the measurement of the tension loading strengths of the inventive adhesive (2-octyl cyanoacrylate with 18-crown-6 polymerization accelerator) per the FDA recommendation. The test method is also intended to compare the tensile strength properties of Dermabond® topical skin adhesive. The test was conducted following ASTM F2258-05. This tension loading method was used to determine strength of adhesives for bonding materials. Two pieces of pig skin were affixed onto the stamp-shaped steel substrate, which were adhered together by the test adhesives. The sample preparation and conditioning are the same as the procedure stated in Example 25. The tensile strength in tension was measured at a constant cross-head speed of 2 mm/min.

As summarized in Table 6, the average tensile strength using tension loading for the inventive adhesive and Dermabond® topical skin adhesive are 14.16 and 10.88 lbs/int, respectively. The standard deviations of stamp tensile strengths for the inventive adhesive and Dermabond® topical skin adhesive are 1.39 and 1.41, respectively, which suggests that the average strength value of the inventive adhesive is higher than that of the Dermabond® product.

TABLE 6

Tensile strength using tension loading of the inventive adhesive and Dermabond ® topical skin adhesive
Strength Properties Using Tension Loading ASTM (F2258-05)

| | lbs/in$^2$ | |
| --- | --- | --- |
| | Example 26 Adhesive | Dermabond ® Product |
| Sample 1 | 14.20 | 10.80 |
| Sample 2 | 14.40 | 11.20 |
| Sample 3 | 12.40 | 8.80 |
| Sample 4 | 16.20 | 12.60 |
| Sample 5 | 12.80 | 11.60 |
| Sample 6 | 14.20 | 13.40 |
| Sample 7 | 16.00 | 10.80 |
| Sample 8 | 13.60 | 9.40 |
| Sample 9 | 15.40 | 10.40 |
| Sample 10 | 12.40 | 9.80 |
| Sample Average | 14.16 | 10.88 |
| Standard Deviation | 1.39 | 1.41 |

Example 27

T-Peel Tensile Strength

The T-peel tensile strength test was evaluated according to ASTM F2256-05. T-peel strength is the average load per unit width of bond line required to yield the separation of two flexible adherends bonded by adhesives. The in vitro test method is intended to provide a means for the measurement of T-peel tensile strength of the inventive adhesive (2-octyl cyanoacrylate with 18-crown-6 polymerization accelerator) as recommended by the FDA. The test method is also intended to compare the peel strength properties of Dermabond® topical skin adhesive. The sample preparation and conditioning were the same as the procedure stated in Example 25. The T-peel tensile strength was measured at a constant cross-head speed of 250 mm/min.

The average T-peel tensile strength for the inventive adhesive and Dermabond® topical skin adhesive are 39.64 and 27.14 lb, respectively, as shown in Table 7. The standard deviations of T-Peel strengths for the inventive adhesive and the Dermabond® product were 4.73 and 2.97, respectively, which suggests that the average T-peel tensile strength value of the inventive adhesive is significantly higher than that of the Dermabond® product.

TABLE 7

T-peel tensile strength of the inventive adhesive and
Dermabond ® topical skin adhesive
Strength Properties Using T-Peel Tension Loading
ASTM (F2256-05)

| | Lbs | |
|---|---|---|
| | Example 27 Adhesive | Dermabond ® topical skin adhesive |
| Sample 1 | 36.20 | 22.20 |
| Sample 2 | 37.80 | 27.80 |
| Sample 3 | 42.60 | 22.60 |
| Sample 4 | 38.80 | 24.80 |
| Sample 5 | 34.20 | 28.40 |
| Sample 6 | 45.80 | 28.80 |
| Sample 7 | 34.20 | 29.40 |
| Sample 8 | 42.00 | 31.20 |
| Sample 9 | 47.80 | 27.60 |
| Sample 10 | 37.00 | 28.60 |
| Sample Average | 39.64 | 27.14 |
| Standard Deviation | 4.73 | 2.97 |

Example 28

Wound Closure Strength

Wound closure strength was measured by following ASTM F2458-05. This test method is intended to provide a means for the measurement of wound closure strength of the inventive adhesive (2-octyl cyanoacrylate with 18-crown-6 polymerization accelerator) as recommended by the FDA. The test method is also intended to compare the wound closure strength of Dermabond® topical skin adhesive. Wound closure strength is the average force required to disrupt wound closed by test adhesives (in this case, adhesion of two pieces of pig skin by the test adhesives was used as the substitute of wound closure). The sample preparation and conditioning were conducted as the procedure stated in Example 25. The wound closure tensile strength was measured at a constant cross-head speed of 50 mm/min.

Table 8 summarizes the wound closure strength of the inventive adhesive and the Dermabond® product. The average wound closure tensile strength for the inventive adhesive and the Dermabond® product are 2.67 lbs and 2.36 lbs, respectively. The standard deviations of tensile strength of wound closure for the inventive adhesive and the Dermabond® product are 0.93 and 0.87, respectively, which suggests that the average wound closure strength value of the inventive adhesive is comparable with that of the Dermabond® product.

TABLE 8

Wound closure strength of the inventive adhesive and
Dermabond ® topical skin adhesive
Strength Properties Using Wound Closure Adhesive &
Sealant Tests ASTM (F2458-05)

| | Lb | |
|---|---|---|
| | Example 28 adhesive | Dermabond ® topical skin adhesive |
| Sample 1 | 1.880 | 1.745 |
| Sample 2 | 2.570 | 1.140 |
| Sample 3 | 3.035 | 1.955 |
| Sample 4 | 4.050 | 2.980 |

TABLE 8-continued

Wound closure strength of the inventive adhesive and
Dermabond ® topical skin adhesive
Strength Properties Using Wound Closure Adhesive &
Sealant Tests ASTM (F2458-05)

| | Lb | |
|---|---|---|
| | Example 28 adhesive | Dermabond ® topical skin adhesive |
| Sample 5 | 2.134 | 3.345 |
| Sample 6 | 1.815 | 3.695 |
| Sample 7 | 3.990 | 2.440 |
| Sample 8 | 3.600 | 1.870 |
| Sample 9 | 1.635 | 3.010 |
| Sample 10 | 1.965 | 1.400 |
| Sample Average | 2.67 | 2.36 |
| Standard Deviation | 0.93 | 0.87 |

Example 29

Lap Shear Tensile Strength

An in-vitro study was used to evaluate the lap shear tensile strength of a microbial sealant based on ASTM method F2255-05. This test method is intended to provide a means for the measurement of the overlap shear tensile strengths of the inventive adhesive (2-octyl cyanoacrylate with 18-crown-6 polymerization accelerator) as recommended by the FDA. Lap shear determines the shear strength of adhesives for bonding materials. Lap shear strength is the force used to separate the two overlapped substrates adhered by adhesives. In this case, two pieces of pig skin attached onto steel substrates were adhered together by the test adhesives. The sample preparation and conditioning are following the procedure stated in Example 25. The lap shear tensile strength was measured at a constant cross-head speed of 5 mm/min. The average lap shear tensile strength for the inventive adhesive and the Dermabond® product are 14.58 lbs/in$^2$ and 15.68 lbs/in$^2$, respectively, as shown in Table 9. The standard deviations of lap shear strengths for the inventive adhesive and the Dermabond® topical skin adhesive are 1.63 and 1.93, respectively, which suggests that the average lap shear tensile strength value of the inventive adhesive is comparable with that of the Dermabond® product.

TABLE 9

Lap shear tensile strength of the inventive adhesive and
Dermabond ® topical skin adhesive
Lap Shear Tensile Loading ASTM (F2255-05)

| | lbs/in$^2$ | |
|---|---|---|
| | Example 29 Adhesive | Dermabond ® topical skin adhesive |
| Sample 1 | 17.80 | 15.60 |
| Sample 2 | 14.20 | 14.00 |
| Sample 3 | 13.60 | 12.80 |
| Sample 4 | 15.40 | 16.60 |
| Sample 5 | 12.20 | 14.20 |
| Sample 6 | 14.20 | 13.60 |
| Sample 7 | 14.60 | 18.40 |
| Sample 8 | 15.40 | 17.20 |
| Sample 9 | 12.60 | 16.60 |
| Sample 10 | 15.80 | 17.80 |

TABLE 9-continued

Lap shear tensile strength of the inventive adhesive and Dermabond ® topical skin adhesive
Lap Shear Tensile Loading ASTM (F2255-05)

| | lbs/in$^2$ | |
|---|---|---|
| | Example 29 Adhesive | Dermabond ® topical skin adhesive |
| Sample Average | 14.58 | 15.68 |
| Standard Deviation | 1.63 | 1.93 |

Example 30

Flexibility

This test method describes the method used to determine the flexibility of an adhesive film bonded to a flexible substrate. Flexibility is evaluated using mandrel bend based on ASTM D4338-97. A natural rubber coated with a film of the test adhesives, properly sized, was folded to form an inverted U-shaped angle over the mandrel, maintaining intimate contact with the non-adhesive side. Using a fresh specimen for each test, the test was repeated with progressively smaller diameter mandrels. The test procedure is listed in the following:

1) Apply the inventive adhesives (2-octyl cyanoacrylate with 18-crown-6 polymerization accelerator; or the Dermabond® topical skin adhesive) onto natural rubber.
2) Store the test specimens and test apparatus at the test conditions for 24 hours.
3) Run the tests in the same environment used to condition the test specimens and test apparatus.
4) Put the largest diameter mandrel in the horizontal operating position in the test frame.
5) Grasp the test specimen between the thumb and forefinger of one hand, with the longest dimension between the fingers. For low-temperature testing, use cotton work gloves to insulate the test specimens from the warm fingers.
6) Lay the flat steel (or other support substrate) of the test specimen tangentially at right angles to the longitudinal axis of the test mandrel.
7) Within 1 s, fold the test specimen with the adhesive side opposite to the mandrel to form an inverted U-shaped angle over the mandrel maintaining intimate contact with the mandrel.
8) Failure is a fracture, or cracking of the adhesive film visible to the naked eye. This can occur at any time during the bending of the adhesive test specimen over the mandrel. Color changes, ripples or blushing, not affecting the tensile properties of the materials, are not considered as failure, but should be reported.
9) Fold a fresh specimen over the next smaller diameter mandrel.
10) Repeat the test five times, using five fresh specimens, on the smallest-diameter mandrel at which failure had not occurred; at least 80% of test specimens must pass.

No sign of cracking, blistering, blushing, fractures, or flaking was observed during the folding test for polymer film of the inventive adhesive and Dermabond® topical skin adhesive. This indicates that both the inventive adhesive and the Dermabond® product are flexible suggesting that the said adhesive and the Dermabond® product are equivalent in terms of flexibility.

Example 31

Viscosity Measurement

The viscosity of the cyanoacrylate compositions were measured by the Brookfield DV-II+ viscometer. The spindle and cup were cleaned with acetone after each measurement. About 0.5 ml of the surgical drape composition was put into the cup and the cup was brought into position and slowly secured with the retaining arm. The motor was turned on after the sample was equilibrated in the cup. The viscosity of the disclosed surgical drape composition was measured in triplicate. Any residue was removed with acetone prior to the next sample measurement.

Example 32

Cure Speed Measurement

Cure speed of the inventive adhesive was measured in vitro on pig skin. Pig skin (4×4 square inch) was prepared by wiping the surfaces of the skin with sterile gauze saturated with isopropanol. All oily substances were thereby removed from the pig skin. The surface was then wiped with sterile gauze to remove the isopropanol. The applicator containing the inventive adhesives was opened and adhesive was permitted to saturate the sponge applicator tip for about 10 seconds prior to application. A thin film was applied to the pig skin after which elapsed time was recorded by a stop watch. Cure time was then recorded by stopping the clock when the film was dry as determined at the point where no liquid transfer occurred when the film was touched with a gloved finger.

Example 33

Surface Coverage

A 2-octyl cyanoacrylate composition with 18-crown-6 polymerization accelerator was applied to pig skins from an applicator until all of the adhesive (0.35 mL) was dispensed. The length and width of the covered areas was measured with electronic digital calipers. These values were used to calculate the surface coverage per applicator. The surface coverage was measured according to the following procedures. Several of pig skins with a dimension of 4×12 inch were prepared by wiping the surfaces of the skin with sterile gauze saturated with isopropanol to make sure that all oily substances were removed from the pig skin. The surface of the skin was wiped dry with gauze. The whole area of the pig skin was covered by diminishing the gap and overlap as much as possible and by keeping the strokes even. The width and length of pig skin covered with adhesive was measured using an electronic digital caliper. The surface area was calculated from the measured width and length. The average surface coverage of the drape composition disclosed in the present invention device was approximately 27.9 inch$^2$.

The foregoing examples and description of the preferred embodiments should be taken as illustrating, rather than as limiting the present invention as defined by the claims. As will be readily appreciated, numerous variations and combinations of the features set forth above can be utilized without departing from the present invention as set forth in the claims. Such variations are not regarded as a departure from the spirit and scope of the invention, and all such variations are intended to be included within the scope of the following claims.

We claim:

1. A sterilized cyanoacrylate adhesive composition comprising
99% or more by weight, based on the weight of the adhesive composition, of 2-octyl cyanoacrylate, mixed together with
a free radical stabilizer,
an anionic vapor phase stabilizer, and
100 to 1000 parts per million, based on the weight of the adhesive composition, of a 18-crown-6 crown ether,
wherein said composition is sterilized by irradiation, and wherein the sterilized composition has a viscosity of 5 to 70 cp following storage for twelve days at 80° C.; and
wherein the composition when cured on a patient's tissue has a water vapor transmission rate from about 950 to about 3000 g/m$^2$/day.

2. The sterilized cyanoacrylate adhesive composition of claim 1, wherein the sterilized composition has a viscosity of 5 to 30 cp following storage for twelve days at 80° C.

3. The sterilized cyanoacrylate adhesive composition of claim 1, wherein said free radical stabilizer is butylated hydroxyl anisole and said anionic vapor phase stabilizer is sulfur dioxide.

4. The sterilized cyanoacrylate adhesive composition of claim 1, wherein the composition has been treated with a particulate agent selected from the group consisting of vinyl pyrrolidone polymers and co-polymers.

5. The sterilized cyanoacrylate adhesive composition of claim 1 wherein the water vapor transmission rate is from about 1000 to about 2500 g/m$^2$/day.

6. The sterilized cyanoacrylate adhesive composition of claim 5 wherein the water vapor transmission rate is from about 1500 to about 2200 g/m$^2$/day.

7. The sterilized cyanoacrylate adhesive composition of claim 1 wherein the cured composition on the patient's tissue has a T-peel loading value of from about 34 to about 48 lbs.

8. The sterilized cyanoacrylate adhesive composition of claim 1 wherein the cured composition on the patient's tissue has a lap-shear tensile strength of from about 12 to about 18 lbs/in$^2$.

9. The sterilized cyanoacrylate adhesive composition of claim 1 wherein the cured composition on the patient's tissue has a tension loading strength of from about 12 to about 16 lbs/in$^2$.

10. The sterilized cyanoacrylate adhesive composition of claim 1 wherein the cured composition on the patient's tissue has a wound closure strength of from about 2 to about 4 lbs.

11. A method of sealing tissue comprising
applying the sterilized cyanoacrylate adhesive composition of claim 1 to a patient's tissue to be sealed; and
allowing the sterilized cyanoacrylate adhesive composition to cure.

12. The method of claim 11 wherein the free radical stabilizer is butylated hydroxyl anisole and the anionic vapor phase stabilizer is sulfur dioxide.

13. The sterilized cyanoacrylate adhesive composition of claim 1, wherein the anionic vapor phase stabilizer is present in the composition at a concentration of less than 50 parts per million.

14. The sterilized cyanoacrylate adhesive composition of claim 13, wherein the anionic vapor phase stabilizer is sulfur dioxide.

15. The sterilized cyanoacrylate adhesive composition of claim 3, wherein the butylated hydroxyl anisole is present in the composition at a concentration of about 200 to about 15000 ppm.

16. A kit, comprising the sterilized cyanoacrylate adhesive composition of claim 1 and an applicator.

* * * * *